US010537579B2

(12) United States Patent
Inomata et al.

(10) Patent No.: US 10,537,579 B2
(45) Date of Patent: Jan. 21, 2020

(54) REJECTION REACTION SUPPRESSANT

(71) Applicants: JUNTENDO EDUCATIONAL FOUNDATION, Bunkyo-ku (JP); KOWA COMPANY, LTD., Nagoya-shi (JP)

(72) Inventors: Takenori Inomata, Bunkyo-ku (JP); Toshinari Funaki, Bunkyo-ku (JP)

(73) Assignees: JUNTENDO EDUCATIONAL FOUNDATION, Bunkyo-ku (JP); KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 15/976,135

(22) Filed: May 10, 2018

(65) Prior Publication Data

US 2018/0325913 A1    Nov. 15, 2018

(30) Foreign Application Priority Data

May 12, 2017    (JP) .................................. 2017-095113

(51) Int. Cl.
*A61K 31/551* (2006.01)
*A61P 27/02* (2006.01)
*A61K 9/08* (2006.01)
*A61K 9/00* (2006.01)

(52) U.S. Cl.
CPC ............ *A61K 31/551* (2013.01); *A61P 27/02* (2018.01); *A61K 9/0048* (2013.01); *A61K 9/08* (2013.01)

(58) Field of Classification Search
CPC .................................................. A61K 31/551
See application file for complete search history.

(56) References Cited

U.S. PATENT DOCUMENTS

2016/0256470 A1* 9/2016 Sawai .................. A61K 31/551
2017/0290840 A1   10/2017 Takahashi et al.

FOREIGN PATENT DOCUMENTS

| JP | 5557408 | 7/2014 |
| JP | 2017-061440 | 3/2017 |
| WO | WO 2016/047647 A1 | 3/2016 |

OTHER PUBLICATIONS

Kitano et al. Cell-injection therapy using Rho kinase inhibitor in a corneal endothelial dysfunction rabbit model. Investigative ophthalmology & visual science Jun. 2013, vol. 54, abstract.*
Okumura et al. Effect of the rho-associated kinase inhibitor eye drop (ripasudil) on corneal endothelial wound healing Investigative Ophthalmology & Visual Science (2016), 57 (3), 1284-1292 Abstract.*
Sunil K. Chauhan, et al., "Levels of Foxp3 in Regulatory T Cells Reflect Their Functional Status in Transplantation," The Journal of Immunology, 2009, pp. 148-153.
Maryam Tahvildari, MD, et al., "In Vivo Expansion of Regulatory T Cells by Low-Dose Interleukin-2 Treatment Increases Allograft Survival in Corneal Transplantation," www.transplantjournal.com, vol. 100, No. 3, Mar. 2016, pp. 525-532.
List of references from Declaration regarding Non-prejudicial Disclosures of Exemptions to Lack of Novelty submitted in JP-2017-095113, filed on May 12, 2017, 3 pages.
Takenori Inomata, et al., "The Effects of Rock Inhibitor K-115 on Graft Survival in Murine Corneal Transplantation," http://www.acs2016seoul.com/program/posters.php, Nov. 12, 2016, 12 Pages.
Takenori Inomata, et al., "The Effects of Rock Inhibitor K-115 on Graft Survival in Murine Corneal Transplantation," The 5th Asia Cornea Society Biennial Scientific Meeting Final Program, Dec. 9, 2016, 10 Pages.
Takenori Inomata, et al., "The Effects of Rock Inhibitor K-115 on Graft Survival in Murine Corneal Transplantation," The 5th Asia Cornea Society Biennial Scientific Meeting, Dec. 9 to 11, 2016, 12 Pages.
Takenori Inomata, et al., Program Abstract, Japan Cornea Conference 2017, Jan. 13, 2017, 6 Pages.
Takenori Inomata, et al., Program Abstract, Japan Cornea Conference 2017, Jan. 27, 2017, 2 Pages.
Takenori Inomata, et al., Program Abstract, Japan Cornea Conference 2017, Feb. 16, 2017, 3 Pages.
Takenori Inomata, et al., Program Abstract, J32nd Asia-Pacific Academy of Ophthalmology Congress, apan Cornea Conference 2017, Feb. 2017, 2 Pages.
Takenori Inomata, et al., Program Abstract, 32nd Asia-Pacific Academy of Ophthalmology Congress, Feb. 2017, 2 Pages.
Takenori Inomata, et al., Program Abstract, 32nd Asia-Pacific Academy of Ophthalmology Congress, Mar. 1 to 5, 2017, 1 Page.

* cited by examiner

*Primary Examiner* — Jennifer M Kim
(74) *Attorney, Agent, or Firm* — Oblon, McClelland, Maier & Neustadt, L.L.P.

(57) ABSTRACT

To provide a novel method for suppressing rejection after corneal transplantation.
The method for suppressing rejection after corneal transplantation includes administering an effective amount of a Rho kinase inhibitor to a patient who needs it.

12 Claims, 8 Drawing Sheets

REJECTION REACTION SUPPRESSANT

BACKGROUND

Technical Field

The present invention relates to a medicament for suppressing rejection after corneal transplantation.

Related Art

Corneal transplantation is the most common organ transplantation performed about 2000 cases annually in Japan and about 40000 cases annually in the United States. In the case of standard corneal transplantation, its graft survival rate is considered to be 90% or higher. However, it has become a problem that rejection occurs in 40 to 90% of high-risk corneas such as corneas with angiogenesis, infection, autoimmune disease, or corneas that require regrafting. Nowadays, the incidence of acute rejection has reduced due to the use of immunosuppressants such as steroid and cyclosporine, and therefore the results of high-risk corneal transplantation have improved. In fact, however, there are still many problems that such immunosuppressants have side effects (e.g., infection, drug toxicity) and are ineffective for chronic rejection. Further, the number of donor corneas is not necessarily sufficient in Japan, and therefore it is clinically important to establish long-term immune tolerance of a transplanted organ (which is a state in which a transplanted organ satisfactorily functions even after discontinuation of administering an immunosuppressant).

As for immune tolerance, regulatory T cells (Tregs) have attracted attention which act to suppress immune responses. It has become clear that in corneal transplantation, reduced expression of Foxp3, which is a gene essential for the differentiation of Tregs, has an influence on rejection because it causes a reduction in the ability to suppress effector T cells that play a major role in rejection, and a reduction in suppressive cytokines (Chauhan S, et al., J Immunol., 182, 148-153 (2009)). It is also known that the survival of a corneal graft is prolonged by amplification of Tregs through administration of low-dose IL-2 (Tahvildari M et al., Transplantation, 100, 525-532 (2016)).

Rho kinase (Rho-associated, coiled-coil containing protein kinase: ROCK) is a serine-threonine kinase having a molecular weight of about 160 kDa, and its gene is preserved widely from lower animals such as nematodes and drosophila to humans. Rho kinase is involved in physiological functions such as cell morphological control, migration, and gene expression control as well as contraction of smooth muscle cells, and Rho kinase inhibitors have been developed as drugs for treatment of cardiovascular diseases etc.

Further, in recent years, Rho kinase inhibitors have been developed also as drugs for topical administration for treatment of ocular diseases such as glaucoma. As a medicament for the treatment of glaucoma/ocular hypertension, "GLANATEC (registered trademark) ophthalmic solution 0.4%" is commercially available which contains, as an active ingredient, ripasudil hydrochloride hydrate (4-fluoro-5-{[(2S)-2-methyl-1,4-diazepan-1-yl]sulfonyl}isoquinoline monohydrochloride dihydrate).

It is known that ripasudil is effective for the treatment of glaucoma/ocular hypertension, and is, in addition, useful for the treatment of ocular fundus diseases (Japanese Patent No. 5557408), for corneal thickness adjustment (WO 2016/047647), and for the prevention and treatment of complications after cataract surgery (JP 2017-61440 A). However, the effects of ripasudil on rejection after corneal transplant are unknown.

SUMMARY

It is an object of the present invention to provide a novel method for suppressing rejection after corneal transplantation.

The present inventors have intensively studied to achieve the above object, and as a result, have found that a Rho kinase inhibitor, especially ripasudil or a salt thereof or a solvate thereof suppresses angiogenesis and inflammatory responses in a transplanted cornea, and promotes the induction of regulatory T cells (Tregs) so that rejection after corneal transplantation is suppressed. This finding has led to the completion of the present invention.

More specifically, the present invention provides the following (1) to (17).

(1) A medicament for suppressing rejection after transplantation of a cornea, containing a Rho kinase inhibitor.

(2) The medicament for suppressing rejection according to (1), wherein the Rho kinase inhibitor is ripasudil or a salt thereof or a solvate thereof.

(3) The medicament for suppressing rejection according to (2), wherein the ripasudil or the salt thereof or the solvate thereof is ripasudil hydrochloride hydrate.

(4) The medicament for suppressing rejection according to (3), wherein the ripasudil hydrochloride hydrate is ripasudil monohydrochloride dihydrate.

(5) The medicament for suppressing rejection according to any one of (1) to (4), which is a liquid preparation.

(6) The medicament for suppressing rejection according to any one of (1) to (5), which is an ophthalmic preparation.

(7) The medicament for suppressing rejection according to any one of (1) to (6), wherein the cornea is a primate cornea.

(8) The medicament for suppressing rejection according to any one of (1) to (7), wherein the cornea is a human cornea.

(9) A method for producing the medicament for suppressing rejection according to any one of (1) to (8), the method including a step of mixing ripasudil or a salt thereof or a solvate thereof and a pharmaceutically-acceptable carrier.

(10) A method for suppressing rejection after transplantation of a cornea, the method including administering an effective amount of a Rho kinase inhibitor to a patient who needs it.

(11) The method according to (10), wherein the Rho kinase inhibitor is ripasudil or a salt thereof or a solvate thereof.

(12) The method according to (11), wherein the ripasudil or the salt thereof or the solvate thereof is ripasudil hydrochloride hydrate.

(13) The method according to (12), wherein the ripasudil hydrochloride hydrate is ripasudil monohydrochloride dihydrate.

(14) The method according to any one of (10) to (13), wherein the Rho kinase inhibitor is administered in a liquid preparation.

(15) The method according to any one of (10) to (14), wherein the Rho kinase inhibitor is administered in an ophthalmic preparation.

(16) The method according to any one of (10) to (15), wherein the cornea is a primate cornea.

(17) The method according to any one of (10) to (16), wherein the cornea is a human cornea.

The present invention provides a medicament for suppressing rejection after corneal transplantation intended to suppress rejection after corneal transplantation for improving a graft survival rate.

The medicament for suppressing rejection after corneal transplantation according to the present invention can be provided in an ophthalmic preparation that imposes reduced burdens on patients.

DETAILED DESCRIPTION

A Rho kinase inhibitor used in the medicament for suppressing rejection according to the present invention is a substance having a Rho kinase inhibitory activity. Examples of such Rho kinase inhibitors include the following compounds having general names or code numbers: compounds such as ripasudil, AR-13324 (chemical name: 4-[(2S)-3-amino-1-(6-isoquinolinylamino)-1-oxo-2-propanyl]benzyl 2,4-dimethylbenzoate), AR-12286 (chemical name: (2RS)-2-(dimethylamino)-N-(1-oxo-1,2-dihydroisoquinolin-6-yl)-2-(thiophen-3-yl)acetamide), AS1892802 (chemical name: N-[(1S)-2-hydroxy-1-phenylethyl]-N'-[4-(4-pyridinyl)phenyl]-urea), DL0805 (chemical name: 5-nitro-1(2)H-indazole-3-carbonitrile), DW1865 (chemical name: 2-(1H-indazol-5-yl)amino-4-methoxy-6-piperazinotriazine), fasudil (chemical name: 1-(5-isoquinolinesulfonyl)homopiperazine), GSK-269962A (chemical name: [N-(3-{[2-(4-amino-1,2,5-oxadiazol-3-yl)-1-ethyl-1H-imidazo[4,5-c]pyridin-6-yl]oxy}phenyl)-4-{[2-(4-morpholinyl)ethyl]oxy}benzamide]), GSK-429286A (chemical name: N-(6-fluoro-1H-indazol-5-yl)-2-methyl-6-oxo-4-[4-(trifluoromethyl)phenyl]-1,4,5,6-tetrahydro-3-pyridinecarboxamide), H-1152 (chemical name: 5-[[(2S)-hexahydro-2-methyl-1H-1,4-diazepin-1-yl]sulfonyl]-4-methyl-isoquinoline), KD025 (SLx-2119) (chemical name: 2-(3-(4-((1H-indazol-5-yl)amino)quinazolin-2-yl)phenoxy)-N-isopropylacetamide), PT-262 (chemical name: 7-chloro-6-piperidin-1-yl-quinoline-5,8-dione), RKI-1447 (chemical name: 1-[(3-hydroxyphenyl)methyl]-3-(4-pyridin-4-yl-1,3-thiazol-2-yl)urea), SAR407899 (chemical name: 6-(piperidin-4-yloxy)isoquinolin-1(2H)-one), SB-772077B (chemical name: (3S)-1-[[2-(4-amino-1,2,5-oxadiazol-3-yl)-1-ethyl-1H-imidazo[4,5-c]pyridin-7-yl]carbonyl]-3-pyrrolidinamine dihydrochloride), SNJ-1656 (Y-39983) (chemical name: (R)-(+)-N-(1H-pyrrolo[2,3-b]pyridin-4-yl)-4-(1-aminoethyl)benzamide), Wf-536 (chemical name: (+)-(R)-4-(1-aminoethyl)-N-(4-pyridyl)benzamide), Y-26732 (chemical name: (R)-(+)-trans-N-(4-pyridyl)-4-(1-aminoethyl)cyclohexanecarboxamide, AMA0076, AMA0428 (3-[2-(aminomethyl)-5-[(pyridin-4-yl)carbamoyl]phenyl]benzoate), BA-1049, BF-66851, BF-66852, BF-66853, KI-23095, AR-13503, AR-13534, INS-117548, LX7101, (1-benzylpyrrolidin-3-yl)-(1H-indazol-5-yl)amine, (1-benzylpiperidin-4-yl)-(1H-indazol-5-yl)amine, N-[2-(4-fluorophenyl)-6,7-dimethoxy-4-quinazolinyl]-N-(1H-indazol-5-yl)amine, N-4-(1H-indazol-5-yl)-6,7-dimethoxy-N-2-pyridin-4-yl-quinazoline-2,4-diamine, and 4-methyl-5-(2-methyl-[1,4]diazepan-1-sulfonyl)isoquinoline and optical isomers thereof, salts thereof, and solvates thereof. Other examples of Rho kinase inhibitors include compounds disclosed in the following patent references: U.S. Pat. No. 4,678,783, Japanese Patent No. 3421217, WO 95/28387, WO 97/23222, WO 98/06433, WO 99/20620, WO 99/61403, WO 00/09162, WO 01/56988, WO 02/076976, WO 02/076977, WO 02/083175, WO 02/100833, WO 03/059913, WO 03/062225, WO 03/062227, WO 2004/009555, WO 2004/022541, WO 2004/039796, WO 2004/108724, WO 2005/003101, WO 2005/034866, WO 2005/037197, WO 2005/037198, WO 2005/035501, WO 2005/035503, WO 2005/035506, WO2005/039564, WO 2005/080394, WO 2005/103050, WO 2006/057270, and WO 2007/026664 and optical isomers thereof, salts thereof, and solvates thereof. Further, other examples of Rho kinase inhibitors include antisense nucleic acids against ROCK, RNA interference-inducing nucleic acids (e.g., siRNAs) against ROCK, dominant negative mutants of ROCK, and expression vectors thereof.

Among these Rho kinase inhibitors, ripasudil, fasudil, AR-13324, AR-12286, Y-39983, and Y-26732 are preferable, and ripasudil is more preferable.

Hereinbelow, ripasudil, which is one of representative compounds as Rho kinase inhibitors, will be described by way of example.

Ripasudil is a compound that has substance P antagonistic activity, leukotriene D4 antagonistic activity, and Rho kinase inhibitory activity. Medicaments containing ripasudil as an active ingredient are produced and marketed as drugs for the treatment of glaucoma and ocular hypertension. Ripasudil can be produced by a known method, for example, by a method as described in WO 99/20620.

Examples of a salt of ripasudil include salts of inorganic acids such as hydrochloric acid, sulfuric acid, nitric acid, hydrofluoric acid, and hydrobromic acid; and salts of organic acids such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, and camphorsulfonic acid, and a salt of hydrochloric acid is particularly preferable.

Ripasudil or a salt thereof can be present not only as a non-solvate but also as a solvate such as a hydrate. Hydrates are preferable, but in the present invention, all crystalline forms and hydrates or solvates are included. A particularly preferable salt of ripasudil is ripasudil monohydrochloride dihydrate.

In the present invention, the "medicament for suppressing rejection after corneal transplantation" refers to a pharmaceutical drug that suppresses the occurrence of rejection in a cornea after transplantation for improving the survival rate of a graft and maintaining the function of the graft. More specifically, the occurrence of rejection in a cornea after transplantation is suppressed by a single action such as suppression of angiogenesis, suppression of inflammatory responses or induction of immune tolerance, or by a combination thereof so that the survival rate of a graft can be improved and the function of the graft can be maintained.

In the present invention, corneal transplantation includes not only penetrating keratoplasty (PKP) but also "partial keratoplasty" in which only the diseased portion is transplanted. Examples of such partial keratoplasty include lamellar keratoplasty (LKP), deep lamellar endothelial keratoplasty (DLEP), Descemet's stripping endothelial keratoplasty (DSEK), anterior lamellar keratoplasty (ALK), deep anterior lamellar keratoplasty (DLKP, DALK), keratoepithelioplasty (KEP), and Descemet's stripping automated endothelial keratoplasty (DSAEK). In Japan, corneal grafts are usually obtained from eyes donated to eye banks. However, a corneal graft obtained by induction of differentiation from stem cells, such as iPS cells, may be used, or various cells of epithelium, Bowman's membrane, stroma, Descemet's membrane, and endothelium constituting a cornea, which are obtained by induction of differentiation from stem cells such as iPS cells, may be used singly or in appropriate combination.

Further, in the present invention, indications of corneal transplantation are impaired vision resulting from a cloudy cornea that cannot be expected to be made transparent by conservative medical treatment and advanced corneal shape abnormality that is difficult to be remedied by a contact lens. Specific examples of such indications include keratoconus, bullous keratopathy, corneal leukoma, corneal herpes, and corneal dystrophy.

In the present invention, the most serious rejection after corneal transplantation is endothelial rejection. However, the rejection after corneal transplantation is not limited to endothelial rejection, and also includes a condition where opacity or exfoliation of a graft is caused by a single factor such as angiogenesis, inflammatory responses, or immune responses or by a combined action thereof so that the normal function of the graft cannot be maintained.

Further, as will be shown in Examples described later, ripasudil used in the present invention increases regulatory T cells (Tregs) that act to suppress immune responses and induces immune tolerance, and therefore can be used as a "medicament for suppressing rejection after transplantation" not only for corneal transplantation but also for other organ transplantations. Examples of target organ transplantation include heart transplantation, lung transplantation, renal transplantation, liver transplantation, pancreas transplantation, small-intestinal transplantation, and hematopoietic stem cell transplantation typified by bone-marrow transplantation.

The "medicament for suppressing rejection after corneal transplantation" according to the present invention is formulated into a dosage form suitable for ocular topical administration by a conventional formulation technique generally used in this field. Preferable examples of such a dosage form include, but are not limited to, liquids such as intra-anterior chamber injections, intraocular irrigating solutions, and ophthalmic solutions. As a preferable preparation, intra-anterior chamber injections and intraocular irrigating solutions are preferable dosage forms from the viewpoint of treatment effect, but place a heavy burden on patients. From the viewpoint of ease of administration, ophthalmic preparations are preferable.

The ophthalmic preparation according to the present invention contains ripasudil or a salt thereof or a solvate thereof as an active ingredient and an acceptable carrier for ophthalmic preparations, and commercially-available "GLANATEC ophthalmic solution 0.4%" may be directly used.

The ophthalmic preparation can be prepared by, for example, dissolving or suspending the above-described desired component in an aqueous solvent such as sterile purified water or physiological saline or an non-aqueous solvent such as vegetable oil such as cotton seed oil, soybean oil, sesame oil, or peanut oil, adjusting the osmotic pressure of the solution or suspension to a predetermined value, and subjecting the solution or suspension to sterilization such as filter sterilization. When an ophthalmic ointment is prepared, an ointment base may be contained in addition to the above-described various components. The ointment base is not particularly limited, and preferable examples thereof include: an oily base such as Vaseline, liquid paraffin, or polyethylene; an emulsion base obtained by emulsifying an oil phase and an aqueous phase with a surfactant or the like; and a water-soluble base including hydroxypropylmethyl cellulose, carboxymethyl cellulose, polyethylene glycol, or the like.

When ripasudil or a salt thereof or a solvate thereof is used for the "medicament for suppressing rejection after corneal transplantation" according to the present invention, its dose depends on the body weight, age, sex, and symptom of a patient, dosage form, and the frequency of administration, and the daily dose of ripasudil in adults is usually from 0.025 to 10000 µg, preferably from 0.025 to 2000 µg, more preferably from 0.1 to 2000 µg, even more preferably from 0.025 to 200 µg, even more preferably from 0.025 to 100 µg.

When the medicament for suppressing rejection after corneal transplantation according to the present invention is used as an ophthalmic preparation, the concentration of its active ingredient may be about 0.0001 to 5 w/v %, preferably about 0.01 to 4 w/v %. The medicament for suppressing rejection after corneal transplantation according to the present invention is preferably continuously administered from the day of corneal transplantation.

Further, the frequency of administration is not particularly limited, but administration is preferably performed once or several times a day. For a liquid ophthalmic preparation, one to several drops may be instilled into the eye per administration.

Examples of an object to which the "medicament for suppressing rejection after corneal transplantation" of the present invention is administered include mammals (e.g., humans, mice, rats, hamsters, rabbits, cats, dogs, cattle, horses, sheep, and monkeys). Preferable examples of mammals include primates such as humans and monkeys. Humans are particularly preferable.

EXAMPLES

Hereinbelow, the present invention will be more specifically described with reference to examples, but the present invention is not limited to these examples.

Example 1

Effects of Ripasudil on Mouse Corneal Transplant Models (1)

Mouse corneal transplant models were prepared in accordance with a method described in a document (J Biol Methods 2015 2(3); e 27, hereinafter referred to as Document A) and used in an experiment. More specifically, allograft corneal transplantation was performed between 6 to 8-week-old donor male C57BL/6 mice and 6 to 8-week-old host male Balb/c mice.

The mice that had received corneal transplantation were divided into three groups (5 mice per group): ocular instillation of PBS twice daily (Group P: control group); ocular instillation of ripasudil twice daily (Group R2); and ocular instillation of ripasudil three times daily (Group R3).

The amount of PBS or ripasudil instilled into one eye per administration was 0.1 μL, and GLANATEC ophthalmic solution 0.4% was used as ripasudil.

After transplantation, the ocular instillation was performed every day until day 56, during which the angiogenesis score and opacity score (each of which was determined by a method described in. Document A) and the survival time of corneal grafts were evaluated with a slit lamp microscope every 7 days. On day 56 that was the final day of the experiment, in addition to the above evaluations, the expression levels of vascular endothelial cells (CD31), vascular endothelial cell growth factor (VEGF-A), and lymph vessels (Lyve-1) in the corneas were measured by real-time-PCR.

Figure 1:
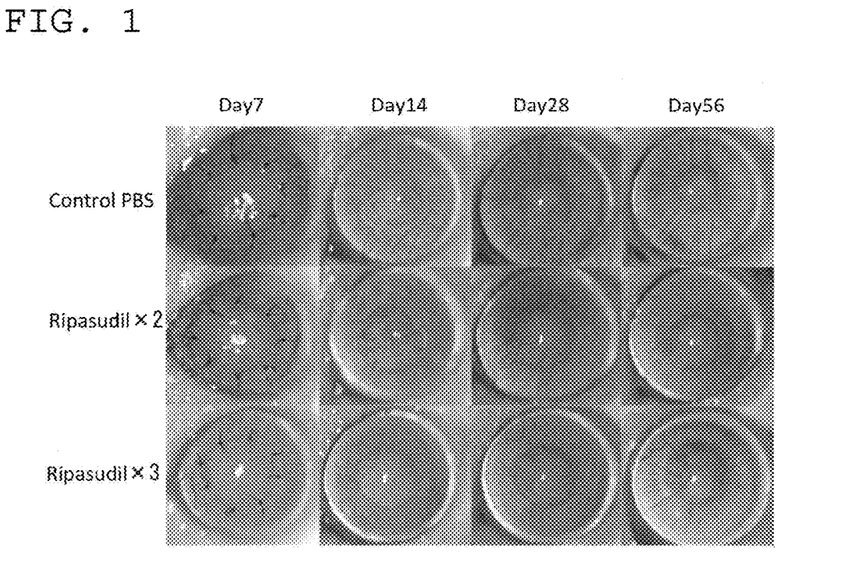
FIG. 1 shows photographs illustrating temporal changes of transplanted mouse corneas to show the effects of ripasudil.
Figure 2:
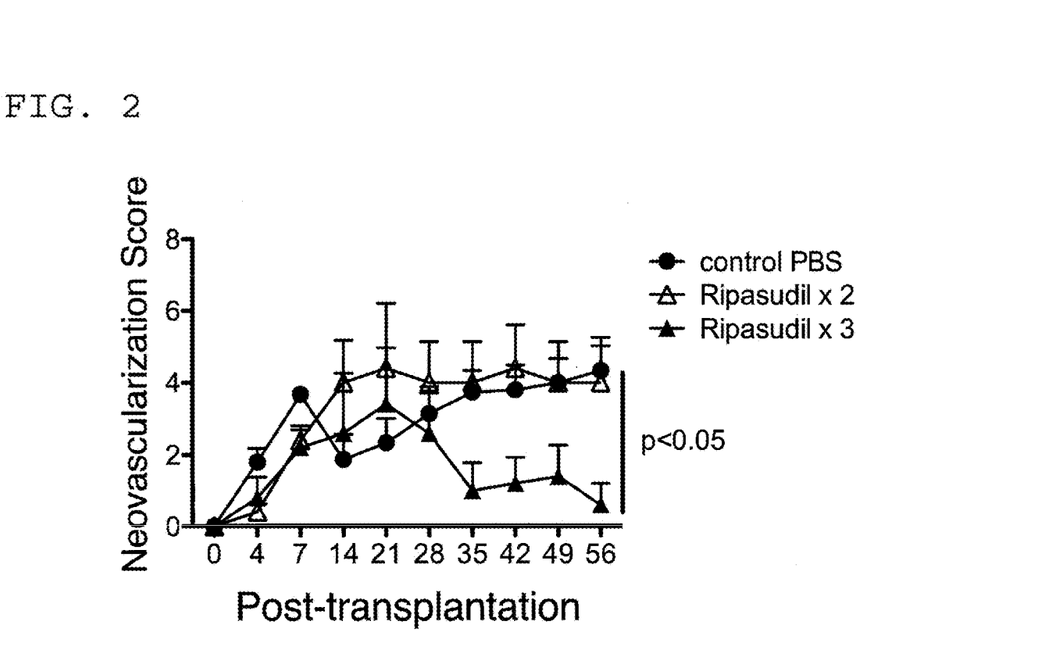
FIG. 2 is a graph illustrating the effect of ripasudil on angiogenesis in transplanted mouse corneas.
Figure 3:
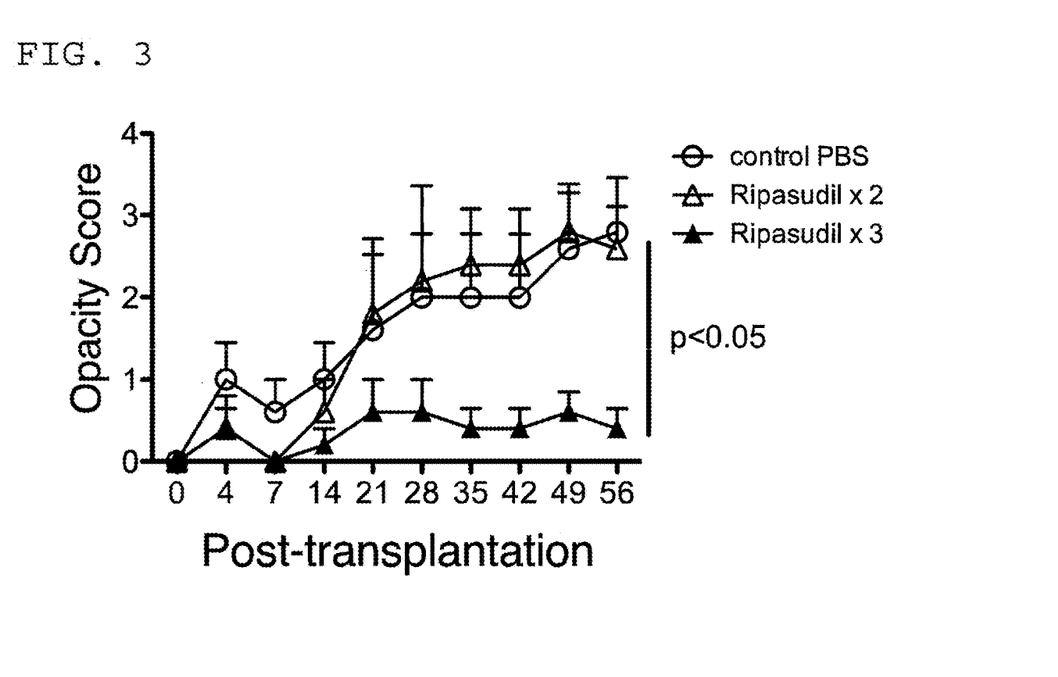
FIG. 3 is a graph illustrating effect of ripasudil on the opacity of transplanted mouse corneas.
Figure 4:
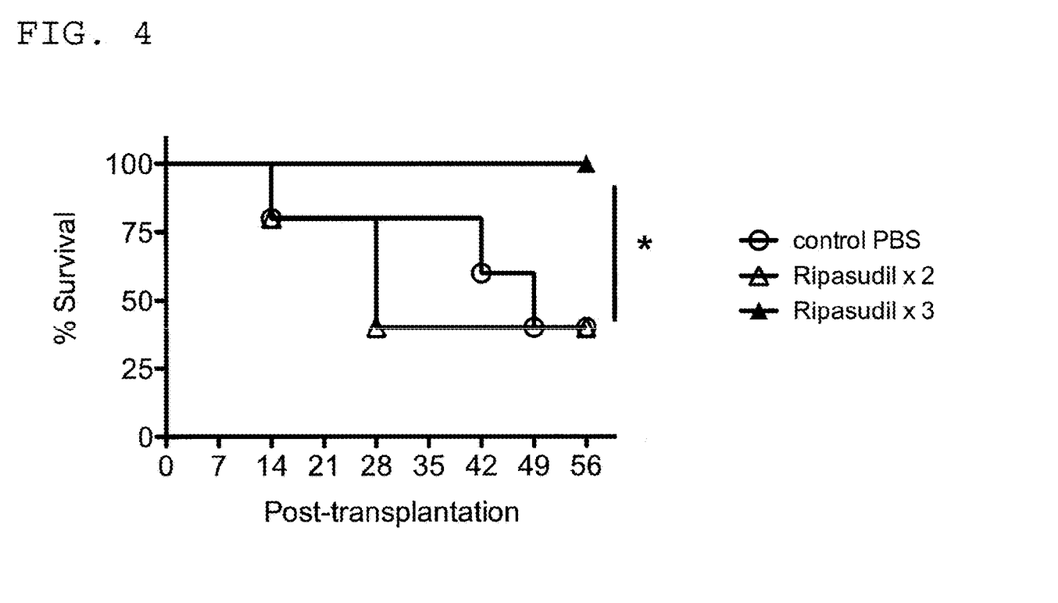
FIG. 4 is a graph illustrating effect of ripasudil on the survival time of transplanted mouse corneas.

The results are shown in FIGS. 1 to 5C. FIG. 1 shows representative photographs of each of the groups taken on day 7, day 14, day 28. and day 56 in the experiment, wherein the upper photographs correspond to Group P, the middle photographs correspond to Group R2, and the lower photographs correspond to Group R3. It can be understood that in Group R3, opacity and angiogenesis were particularly suppressed, and transparency was maintained until day 56. Further, as supported by the results of evaluation scores shown in FIG. 2 (angiogenesis score) and FIG. 3 (opacity score) and the results shown in FIG. 4 (survival time), the angiogenesis score and the opacity score were both significantly lower in Group R3 than in Group P, and the survival time was also significantly prolonged in Group R3 (two-way ANOVA test, Bonferroni's Multiple Comparison Test, *: $p<0.05$).

Figure 5A:
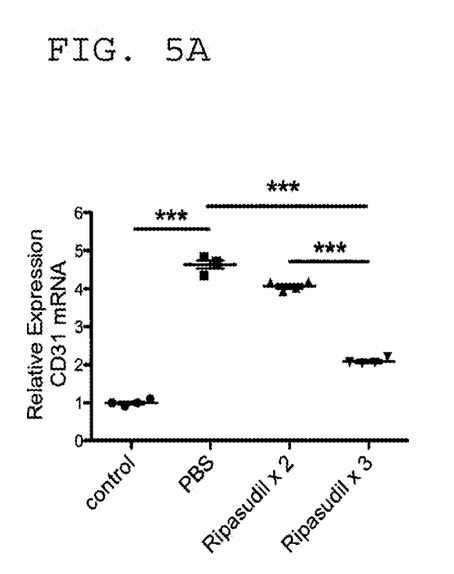
FIGS. 5A, 5B and 5C show graphs illustrating effect of ripasudil on the expression levels of CD31 (FIG. 5A), VEGF-A (FIG. 5B) and Lyve-1 (FIG. 5C) in transplanted mouse corneas on day 56 after transplantation.
Figure 5B:
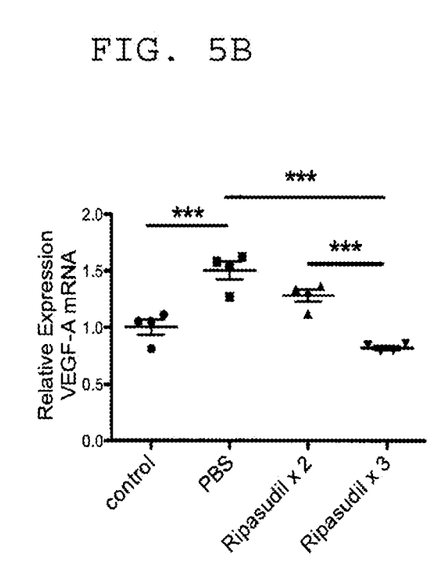
Figure 5C:
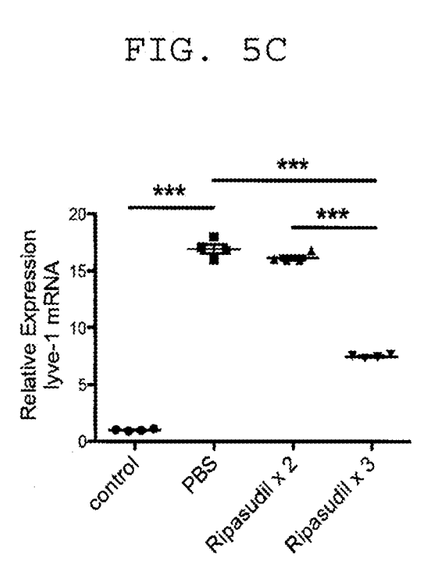
Figure 6A:
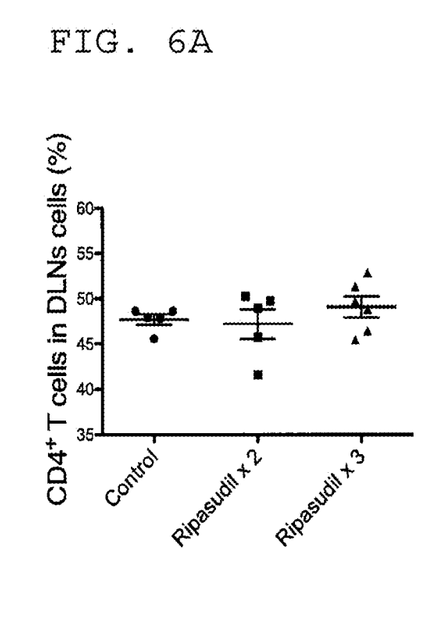
FIGS. 6A, 6B, 6C show graphs illustrating ratio of $CD4^+$ T cells (FIG. 6A) and the effect of ripasudil on the expression of IFNγ (FIG. 6B) and IL-17 (FIG. 6C) in mouse cervical lymph nodes on day 14 after transplantation.
Figure 6B:
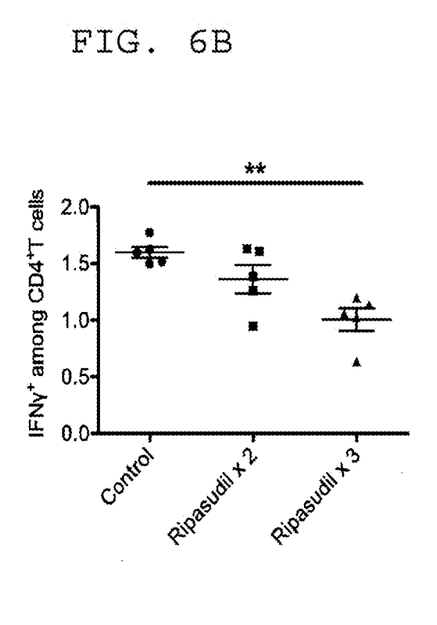
Figure 6C:
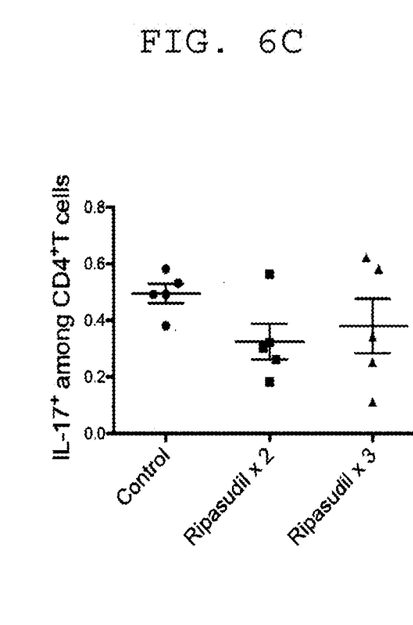
Figure 7A:
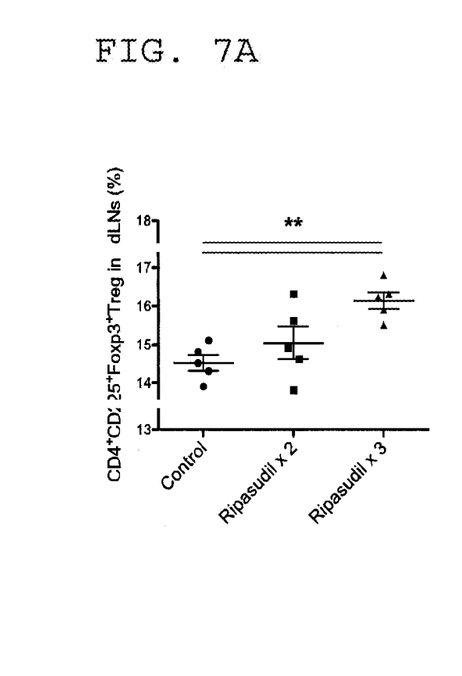
FIGS. 7A, 7B, 7C show graphs illustrating ratios of Tregs (FIG. 7A) and exTregs (FIG. 7B) and effect of ripasudil on the expression of Foxp3 (FIG. 7C) in mouse cervical lymph nodes on day 14 after transplantation.
Figure 7B:
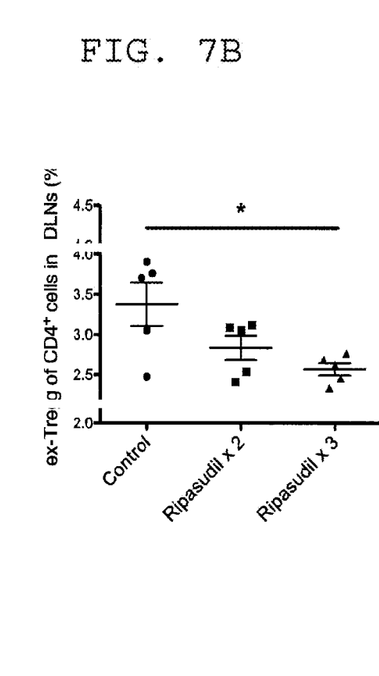
Figure 7C:
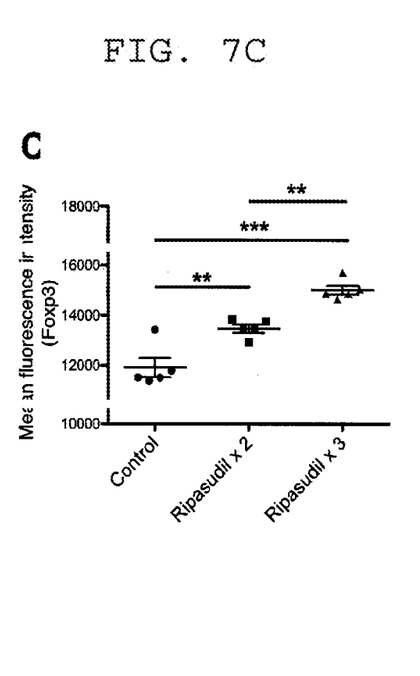
Figure 8A:
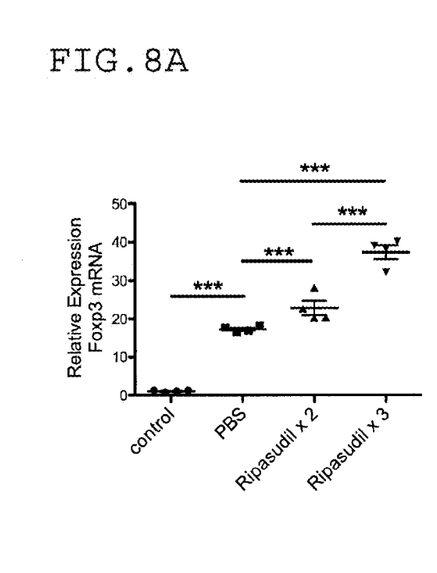
FIGS. 8A, 8B, 8C show graphs illustrating effect of ripasudil on the expression of foxp3 (FIG. 8A), IL-10 (FIG. 8B), and TGFβ1 (FIG. 8C) in transplanted mouse corneas on day 14 after transplantation.
Figure 8B:
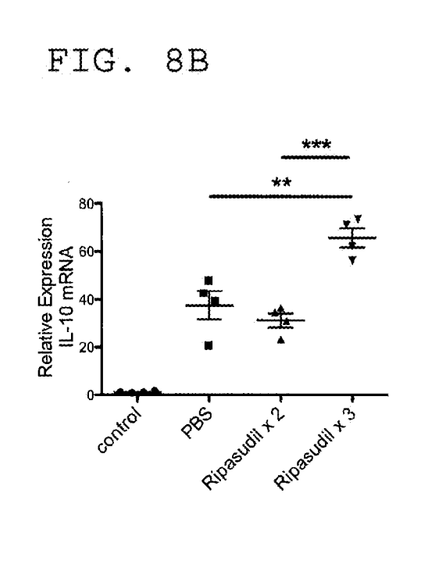
Figure 8C:
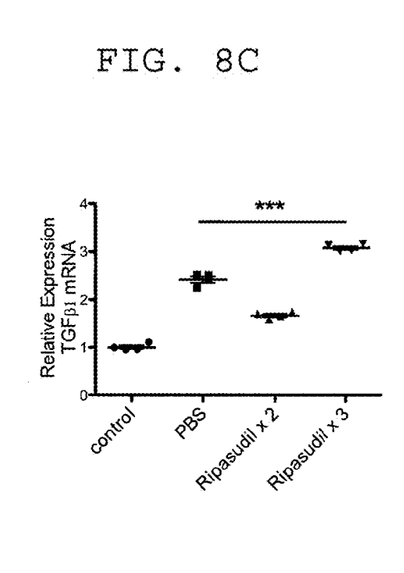

Further, as shown in FIGS. 5A, 5B and 5C. CD31 (FIG. 5A). VEGF-A (FIG. 5B), and Lyve-1 (FIG. 5C) expression levels on day 56 were all significantly lower in Group R3 than in Group P (one-way ANOVA, Bonferroni's Multiple Comparison Test, ***: $p<0.001$).

From the above results, it was found that ocular instillation of ripasudil was useful for the establishment of a transplanted cornea.

Example 2

Effects of Ripasudil on Mouse Corneal Transplant Models (2)

Mouse corneal transplant models were prepared (surgery), divided into groups (Group P, Group R2, and Group R3), and treated (ocular instillation) in the same manner as in Example 1. On day 14 after transplantation, cervical lymph node cells were collected, and CD4$^+$ T cells, the expression levels of inflammatory cytokines IFNγ and IL-17, CD4$^+$CD25$^+$Foxp3$^+$ regulatory T cells (Tregs) involved in immune tolerance, CD4$^+$CD25$^+$Foxp3$^+$ regulatory T cells (exTregs), and the expression level of Foxp3 (Mean Fluorescein Intensity, MFI) were measured by flow cytometry (FACS). Further, on day 14 after transplantation, the expression levels of foxp3, IL-10, and TGFβ1 in the corneas were also measured by a real-time PCR (qPCR).

The results are shown in FIGS. 6A-8C. In Group R3, a significant reduction in inflammatory cytokine IFN-γ was confirmed in the cervical lymph node cells collected on day 14 after transplantation (FIG. 6B). Further, in Group R3, CD4$^+$CD25$^+$Foxp3$^+$ regulatory T cells (Tregs) that act to suppress immune responses to corneal transplantation were significantly increased in the cervical lymph node cells collected on day 14 after transplantation (FIG. 7A), and in both Group R2 and Group R3, Foxp3 that is a transcription factor for Tregs was significantly increased (FIG. 7C). On the other hand, in Group R3, CD4$^+$CD25$^+$Foxp3$^-$ regulatory T cells (exTregs) were significantly reduced (FIG. 7B) (one-way ANOVA, Bonferroni's Multiple Comparison Test, *: $p<0.05$, : $p<0.01$, *: $p<0.001$).

Further, in the corneas on day 14 after corneal transplantation, the expression of foxp3 was significantly increased in Group R2 and Group R3 (FIG. 8A), and the expressions of IL-10 (FIG. 8B) and TGFβ1 (FIG. 8C) were both significantly increased in Group R3 (one-way ANOVA, Bonferroni's Multiple Comparison Test, : $p<0.01$, *: $p<0.001$).

From the above results, it was found that ocular instillation of ripasudil induced regulatory T cells (Tregs) in the transplanted corneas so that immune responses were suppressed.

Example 3

Effects on Transplanted Human Cornea

Figure 9:
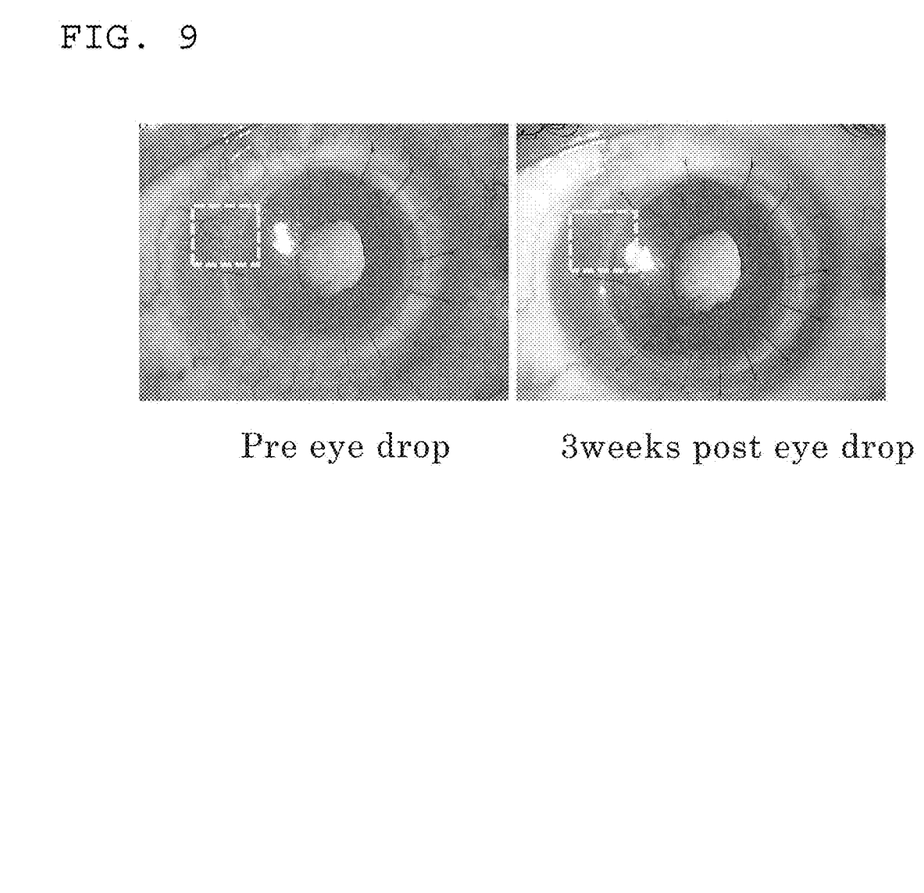
FIG. 9 shows photographs illustrating effect of ripasudil on angiogenesis in a transplanted human cornea.
Figure 10:
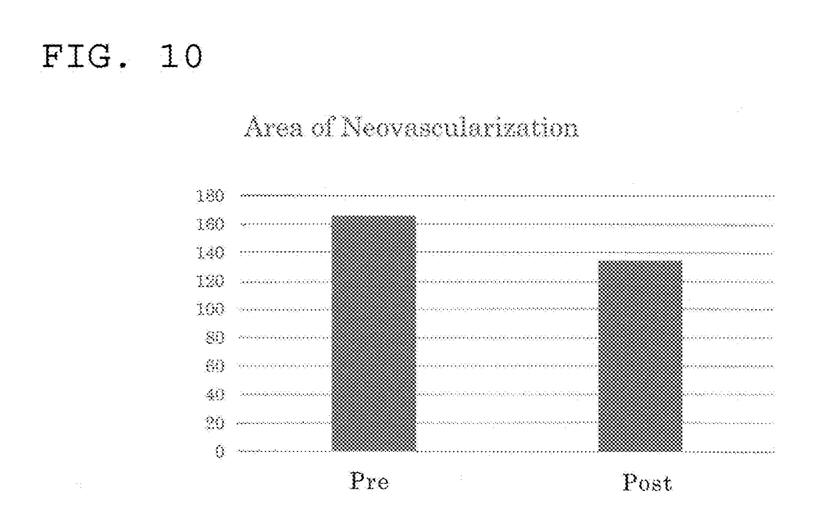
FIG. 10 is a graph illustrating effect of ripasudil on angiogenesis in a transplanted human cornea as a score.

Corneal transplantation was performed in a case of corneal perforation resulting from corneal herpes (male aged 69 years), and as a result, severe hyperemia was observed one month after surgery, and vascularization was observed also in a corneal graft. Peripheral anterior synechia was observed, and secondary glaucoma was observed, and therefore GLANATEC ophthalmic solution 0.4% was prescribed. After 3 weeks from the start of ocular instillation, as shown in FIG. 9, angiogenesis was suppressed. FIG. 10 shows the numerical result of analysis of new blood vessels within a yellow dotted frame shown in FIG. 9 with the use of Image J. FIG. 10 also supported that ripasudil had the effect of suppressing angiogenesis.

What is claimed is:

1. A method for suppressing rejection after transplantation of a cornea, the method comprising:
    administering an effective amount of a Rho kinase inhibitor to a patient in need thereof,
    wherein the Rho kinase inhibitor is ripasudil, a salt thereof or a solvate thereof.

2. The method according to claim 1 wherein the ripasudil, the salt thereof or the solvate thereof is ripasudil hydrochloride hydrate.

3. The method according to claim 2, wherein the ripasudil hydrochloride hydrate is ripasudil monohydrochloride dihydrate.

4. The method according to claim 1, wherein the Rho kinase inhibitor is administered in a liquid preparation.

5. The method according to claim 1, wherein the Rho kinase inhibitor is administered in an ophthalmic preparation.

6. The method according to claim 1, wherein the cornea is a primate cornea.

7. The method according to claim 1, wherein the cornea is a human cornea.

8. The method according to claim 1, wherein a daily dosage of the Rho kinase inhibitor administered is from 0.025 to 10,000 μg per day.

9. The method according to claim 5, wherein the Rho kinase inhibitor is administered once to several times a day.

10. The method according to claim 9, wherein the Rho kinase inhibitor is administered several times a day.

11. The method according to claim 5, wherein a concentration of the Rho kinase inhibitor administered is from 0.0001 to 5 w/v %.

12. The method according to claim 5, wherein a concentration of the Rho kinase inhibitor administered is from 0.01 to 4 w/v %.

* * * * *